(12) United States Patent
Kuchler

(10) Patent No.: US 7,374,542 B2
(45) Date of Patent: May 20, 2008

(54) NONINVASIVE BLOOD PRESSURE DETERMINATION METHOD AND APPARATUS

(75) Inventor: Gert Kuchler, Kist (DE)

(73) Assignee: SOMNOmedics GmbH & Co. KG, Kist (DE)

( * ) Notice: Subject to any disclaimer, the term of this patent is extended or adjusted under 35 U.S.C. 154(b) by 262 days.

(21) Appl. No.: 11/364,174

(22) Filed: Mar. 1, 2006

(65) Prior Publication Data

US 2006/0217616 A1   Sep. 28, 2006

(30) Foreign Application Priority Data

Mar. 23, 2005   (DE) ...................... 10 2005 014 048

(51) Int. Cl.
*A61B 5/02* (2006.01)
*A61B 5/04* (2006.01)

(52) U.S. Cl. ........................ 600/485; 600/500; 600/509

(58) Field of Classification Search ...................... None
See application file for complete search history.

(56) References Cited

U.S. PATENT DOCUMENTS

| 4,807,638 | A |   | 2/1989 | Sramek |          |
|-----------|---|---|--------|--------|----------|
| 5,603,329 | A | * | 2/1997 | Hosaka et al. | 600/493 |
| 5,709,212 | A |   | 1/1998 | Sugo et al. |       |
| 5,743,267 | A | * | 4/1998 | Nikolic et al. | 600/483 |
| 5,785,659 | A |   | 7/1998 | Caro et al. |        |
| 5,865,755 | A |   | 2/1999 | Golub |              |
| 6,511,436 | B1 |  | 1/2003 | Asmar |              |
| 6,599,251 | B2 |  | 7/2003 | Chen et al. |        |
| 6,648,828 | B2 | * | 11/2003 | Friedman et al. | 600/506 |

FOREIGN PATENT DOCUMENTS

| DE |       35333912 C2 | 4/1987 |
| DE |      100 61 189 A1 | 6/2002 |
| DE |      102 49 863 A1 | 5/2004 |
| EP |        0 467 853 B1 | 1/1992 |
| WO |        WO 98/25516 | 6/1998 |

\* cited by examiner

*Primary Examiner*—Robert L. Nasser, Jr.
*Assistant Examiner*—Patricia C Mallari
(74) *Attorney, Agent, or Firm*—Browdy and Neimark

(57) ABSTRACT

The method and the apparatus serve for non-invasively determining the blood pressure of a patient. An electrical cardiac potential measurement signal and a pulse-pressure-wave measurement signal are detected which, starting from the heart, propagate within the blood vessels as far as to a pulse-feeling location. A pulse-pressure-wave propagating time between the heart and the pulse-feeling location is determined, based on the electrical measurement signal and the pulse measurement signal. The blood pressure is determined by the aid of a function interrelationship on the basis of the propagating time, with the function interrelationship comprising a first portion that specifies the active elasticity behaviour of the blood vessels, and a second portion that specifies the passive electricity behaviour of the blood vessels. In this way, especially accurate blood pressure determination is rendered possible.

10 Claims, 3 Drawing Sheets

NONINVASIVE BLOOD PRESSURE DETERMINATION METHOD AND APPARATUS

BACKGROUND OF THE INVENTION

1. Field of the Invention

The invention relates to a method and an apparatus for the noninvasive determination of a patient's blood pressure. In the method, an electrical cardiac-potential measurement signal and a pulse measurement signal of a pulse pressure wave which, starting from the heart, propagates within the blood vessels are recorded at a pulse-feeling location; and, from the electrical measurement signal and the pulse measurement signal, a propagating time is determined of the pulse pressure wave between the heart and the pulse-feeling location. The apparatus comprises an ECG sensor for the detection of an electrical cardiac-potential measurement signal, a pulse sensor for the detection of a pulse measurement signal of a pulse pressure wave which, starting from the heart, propagates within the blood vessels to a pulse-feeling position where the pulse sensor is disposed; and an evaluation unit for determining, from the electrical measurement signal and the pulse measurement signal, a propagating time of the pulse pressure wave between the heart and the pulse-feeling position.

2. Background Art

A method of the generic type has been known from WO98/25516 A1 and an apparatus of the species from U.S. Pat. No. 5,709,212. In the known method, blood pressure is computed as a linear function of the determined propagating time of the pulse pressure wave; in the known apparatus, however, it is computed as a quadratic function of a pulse-pressure-wave velocity i.e., substantially of the reciprocal value of the determined propagating time.

DE 102 49 863 A1 also describes a blood pressure determination method and apparatus of the generic type, with any details on the function interrelationship between the determined propagating time of the pulse pressure wave and blood pressure missing.

U.S. Pat. No. 6,599,251 B2 and DE 100 61 189 A1 further disclose methods of noninvasive blood pressure determination, determining a difference in propagating time between two pulse pressure waves which are recorded at two different pulse-feeling locations. The further evaluation uses a non-linear interrelationship between the determined difference of propagating time and required blood pressure. Mention is made of a logarithmic, a potential and an exponential interrelationship.

All those known blood pressure determination methods and apparatuses are in part more suitable than conventional methods and apparatuses which are based for example on the Riva-Rocci principle. Inflation of an arm cuff can be dropped, precluding any undesirable effect, accompanied there-with, on the circuit and on the blood pressure to be measured. Moreover, it is less interfering with a patient. Nevertheless, the mentioned, familiar blood pressure determination methods and apparatuses sometimes furnish blood pressure values that are too vague.

SUMMARY OF THE INVENTION

It is an object of the invention to specify a method of the type mentioned at the outset that offers the possibility of more accurate blood pressure determination.

This object is attained by a method according to which the blood pressure is determined by means of a function interrelationship, based on the propagating time, with the function interrelationship comprising a first portion which describes the active elasticity behaviour of the blood vessels and a second portion which describes the passive elasticity behaviour of the blood vessels.

According to the invention, at least two different portions are considered in the function interrelationship that blood pressure determination is based on. The first, active portion reflects the active or contractile elasticity behaviour of the blood vessels. That behaviour is conditioned by myofilament action and by triggering with the aid of neural and humoral components. The second, passive portion, however, reflects the passive elasticity behaviour of the blood vessels which is in particular due to the connective tissue. Both portions enter into the function interrelationship in particular additively, respectively describing a nonlinear relationship between the determined propagating time of the pulse pressure wave and the blood pressure. Preferably, the first, active portion comprises a product resulting from the reciprocal value of the propagating time and an exponential of the propagating time. The second, passive portion preferably contains a potential of the propagating time.

All in all, the function interrelationship according to the invention describes the real physiological relations that control the propagation of the pulse pressure wave in the blood vessels clearly better than the approaches used in the known methods. That is due to the purposeful and, in particular, individual consideration of the contractile as well as the passive elasticity behaviour of the blood vessels. In this way, the method according to the invention obtains clearly more accurate results in blood pressure determination than any prior art methods.

In keeping with the invention, blood pressure determination involves an additional calibration portion in the function interrelationship. The calibration portion is determined in particular by means of conventional, in particular oscillometric or Riva-Rocci-based, calibration blood pressure determination by the aid of an inflatable cuff. Favorably, a single calibration blood pressure determination will do. There is no need for a patient, as in other methods, to be put into an additional, second blood pressure condition (for instance exercise condition), which is sometimes not possible without jeopardizing the patient. Moreover, the calibration blood pressure determination can take place at any instant i.e., prior to, during or even after the actual blood pressure determination the results of which can be corrected even subsequently, based on the data of the calibration blood pressure determination. Calibration blood pressure determination can take place automatically or manually.

Preferably, the calibration blood-pressure signal is received together with an electrical cardiac voltage measurement signal and a pulse measurement signal of the pulse pressure wave, which raises the accuracy of calibration and thus the accuracy of blood pressure that is determined at a later time. Based on the electrical measurement signal and the pulse measurement signal, an uncalibrated blood pressure value is determined by means of the first and second portion of the function interrelationship, the uncalibrated blood pressure value, together with the measured calibration pressure signal, entering into the calibration portion of the function interrelationship.

In keeping with another advantageous embodiment, a patient's height is taken into account in blood pressure determination. This still increases the accuracy of the method. This is a simple and rather accurate way of determining the distance covered by the pulse pressure wave. A patient's weight may be admitted by alternative or in completion.

In keeping with a preferred embodiment, the electrical measurement signal and the pulse measurement signal are detected virtually at the same place i.e., in direct vicinity to each other. For example, the ECG sensor, used therefor, and the pulse sensor can be accommodated in a joint detection module. Such a detection module is intended to be applied in particular to a patient's limb, finger, toe or ear, in which case a reduce number of individual sensors must be attached to a patient, meaning agreeably reduced interference. Moreover, such a close-proximity detection of the electric measurement signal and the pulse measurement signal helps preclude measurement errors.

Another object of the invention resides in that an apparatus of the type mentioned at the outset is specified, allowing more accurate blood pressure determination.

That object is attained in an apparatus according to which the evaluation unit is designed for determining the blood pressure, based on the propagating time, by means of a function interrelationship which comprises a first portion that describes the active elasticity behaviour of the blood vessels and a second portion that describes the passive elasticity behaviour of the blood vessels.

The apparatus according to the invention and its embodiments substantially offer the same advantages as described above in connection with the method according to the invention and the variants thereof.

Further features, advantages and details of the invention will become apparent from the ensuing description of exemplary embodiments, taken in conjunction with the drawing.

DESCRIPTION OF PREFERRED EMBODIMENTS

Figure 1:
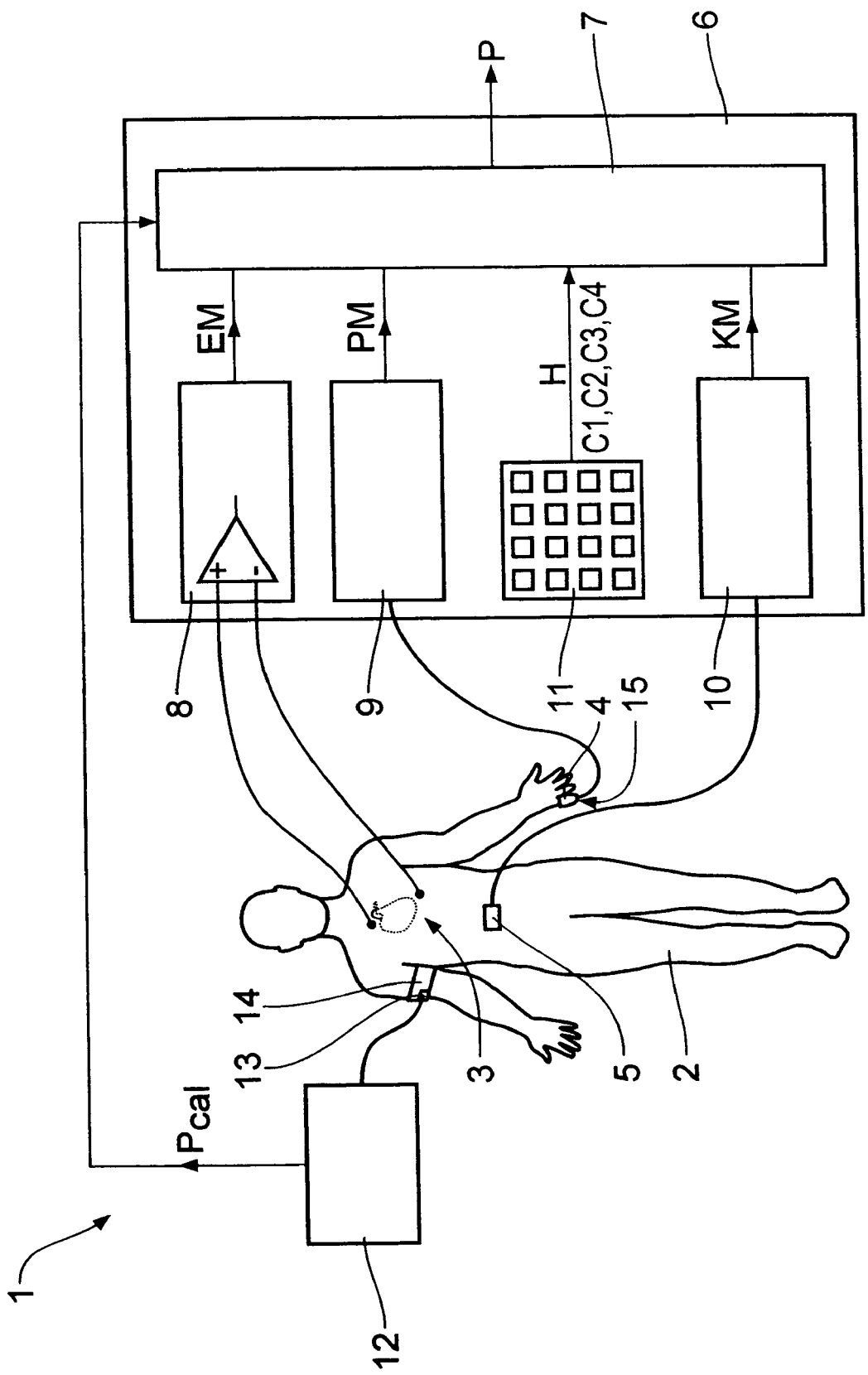
FIG. 1 is an illustration of a block diagram of an embodiment of a blood pressure gauge for noninvasive determination of a patient's blood pressure.

Parts that correspond to one another have the same reference numerals in FIGS. 1 to 4.

FIG. 1 shows an embodiment of a blood pressure gauge 1 for the noninvasive determination of a patient's-2 blood pressure P. It comprises an ECG sensor 3 with at least two recording electrodes, a pulse sensor 4 in the form of a pulse oximeter, and an optional body-position sensor 5 in the form of a three-positional switch, which are connected to an evaluation unit 6. The evaluation unit 6 comprises several components. In addition to a computation unit 7, specific sub-units are provided for each of the connected sensors i.e., an ECG sub-unit 8, a pulse-oximeter sub-unit 9 and a body-position sub-unit 10. Those components of the evaluation unit 6 need not necessarily be physically separated. They may also be implemented as sub-programs of software running on a signal- or micro-processor in the evaluation unit 6. The evaluation unit 6 further comprises input means 11.

A calibration unit 12 with a conventional blood-pressure sensor 13 can be connected to the evaluation unit 6 at least temporarily. In the embodiment, the blood-pressure sensor 13 is a Riva-Rocci blood-pressure sensor, having an inflatable arm cuff 14. In another embodiment (not shown), the calibration unit 12 is a part of the evaluation unit 6. Yet another embodiment is conceivable, in which a calibration blood-pressure value $P_{cal}$ is fed via input means 11 into the evaluation unit 6.

In the embodiment according to FIG. 1, the ECG sensor 3 is disposed on a patient's-2 chest in direct proximity to the heart. The pulse sensor 4 is mounted on a pulse-feeling location 15, on a finger of the patient 2 in the exemplary embodiment. Another pulse-feeling location, for example on the ear, toe or any other limb, is possible just as well. Moreover, the pulse sensor 4 may be embodied as a pressure sensor or ultrasonic sensor instead of a pulse oximeter.

Figure 2:
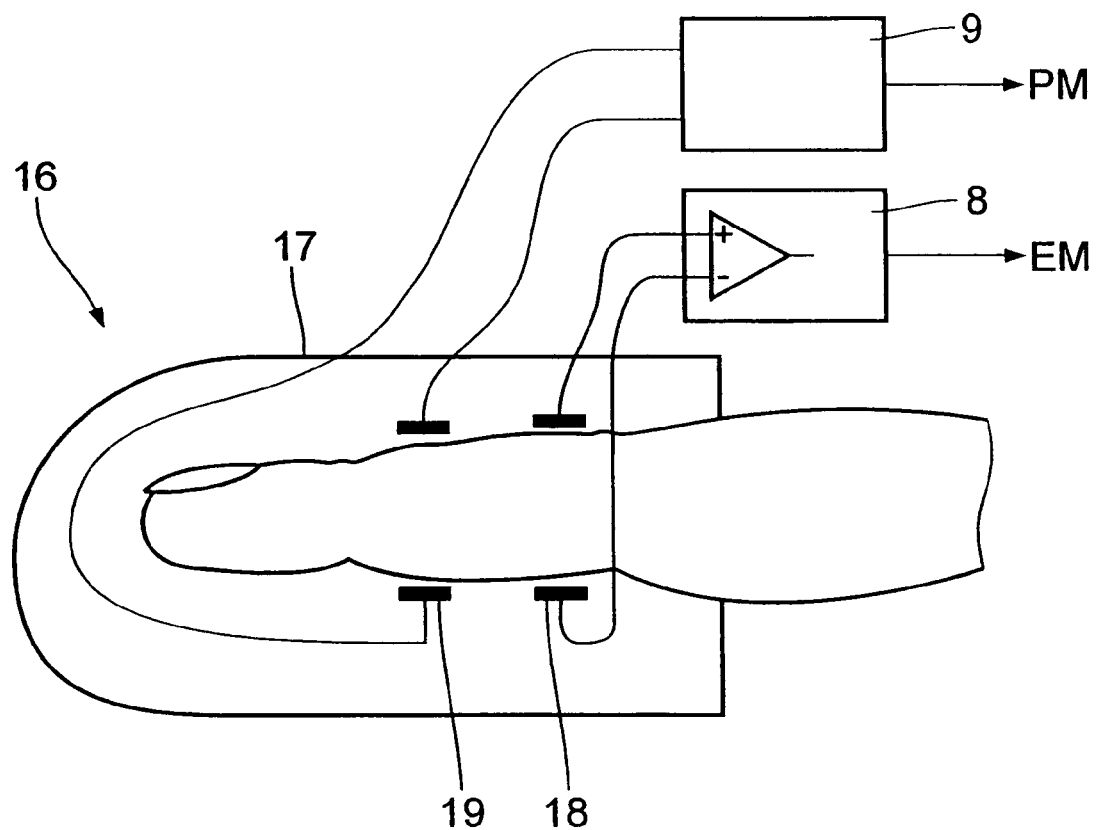
FIG. 2 is an illustration of an exemplary embodiment of a detection module for joint use in a blood pressure gauge according to FIG. 1, detecting an electrical cardiac potential measurement signal and a pulse measurement signal of a pulse pressure wave.

FIG. 2 illustrates an advantageous embodiment of a joint detection module 16. An ECG sensor 18 and a pulse sensor 19 are accommodated in a housing 17 in the form of push-on finger cap, which particularly reduces the space required. The pulse sensor 19 is a pulse oximeter.

Figure 3:
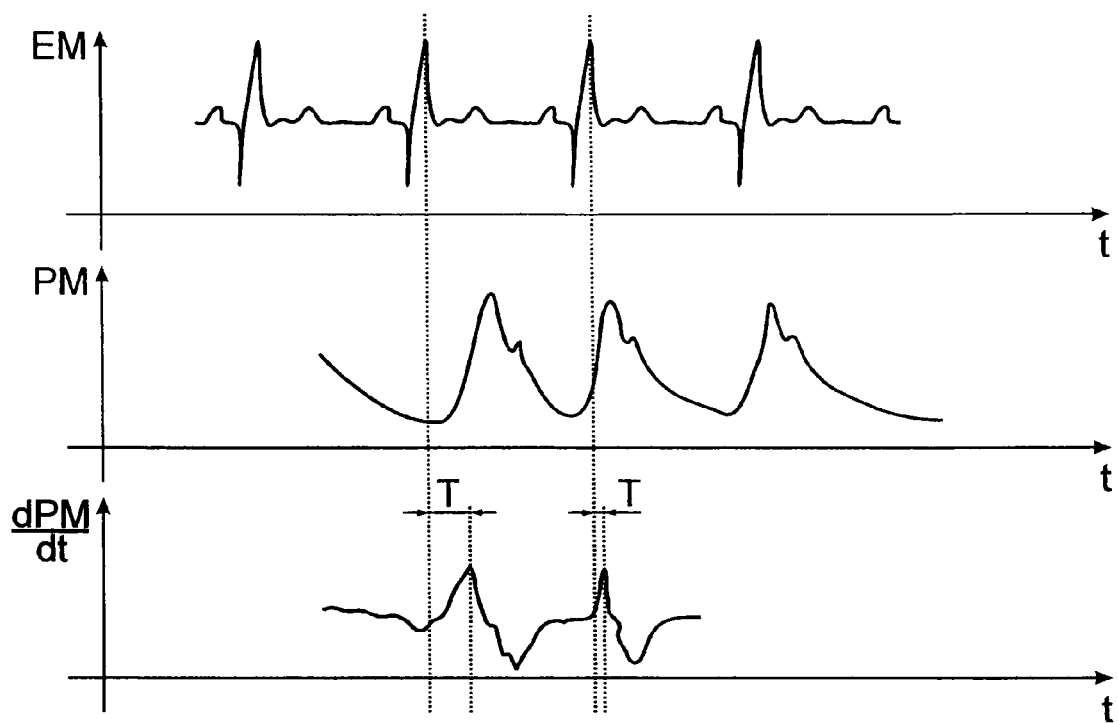
FIG. 3 is a graphic of signal leads detected, or derived, within the scope of the blood pressure gauge of FIG. 1.

The mode of operation of the blood pressure gauge 1 is going to be explained in detail below, also taken in conjunction with the diagrams seen in FIGS. 3 and 4.

From the signals detected by the ECG sensor 3, the ECG sub-unit 8 produces an electrical cardiac voltage measurement signal EM (see diagram at the top of FIG. 3) which is fed into the computation unit 7 for further processing. The pulse sensor 4 detects a pulse pressure wave which passes the pulse-feeling location 15 and, proceeding from the patient's-2 heart, propagates within the blood vessels. Correspondingly, the pulse-oximeter sub-unit 9, in combination with the pulse sensor 4 of the computation unit 7, furnishes a pulse measurement signal PM (see diagram in the middle of FIG. 3). The body-position sub-unit 10, in combination with the body-position sensor 5, emits a body-position signal KM to the computation unit 7.

In the evaluation unit 6, in particular in the computation unit 7, a propagating time T of the pulse pressure wave between a patient's-2 heart and the pulse-feeling location 15 is determined, based on the electrical measurement signal EM and the pulse measurement signal PM. If necessary, the pulse measurement signal PM can be subjected to signal preparation prior to this processing job. It can be smoothed or fitted in particular by means of an approximation process.

The propagating time T used is the difference between the moment of the so-called R-wave in the electrical measurement signal EM and the moment of maximal ascent in the pulse measurement signal PM. For that latter moment to be determined more easily, the time derivative of the pulse measurement signal PM is formed (see diagram at the bottom of FIG. 3). The required propagating time T can then be determined easily by chronological comparison of the maximums in the measurement signal EM and the time derivative of the pulse measurement signal PM. The respective propagation times T, thus determined, for two successive heartbeat cycles are plotted in FIG. 3.

Based on this propagating time T, the computation unit 7 calculates an instantaneous systolic blood pressure P in [mmHg] by means of the function interrelationship $$P = C1 \cdot \frac{D}{T} \cdot e^{C2 \cdot \frac{D}{T}} + C3 \cdot \left(\frac{D}{T}\right)^{C4} + (P_{cal} - P_0) = \quad (1)$$
$$= C1 \cdot v \cdot e^{C2 \cdot v} + C3 \cdot v^{C4} + (P_{cal} - P_0)$$

with D being an approximate distance in [cm] which the pulse pressure wave covers between the heart (left ventricle) and the pulse-feeling location 15; with T being the propagating time of the pulse pressure wave in [ms]; with C1, C2, C3, C4 being a given or selectable parameter; with $P_0$ being a determined, uncalibrated blood pressure value in [mmHg]; with $P_{cal}$ being a calibration blood pressure value in [mmHg]; and with v being a pulse-pressure-wave velocity in [cm/ms].

An especially favorable parameter set consists in C1 assuming the value 700, C2 the value (−1), C3 the value 766000, and C4 the value 9. The function relationship of equation (1) then obtains the special form:

$$P = 700 \cdot \frac{D}{T} \cdot e^{-\frac{D}{T}} + 766000 \cdot \left(\frac{D}{T}\right)^9 + (P_{cal} - P_0) = \quad (2)$$
$$= 700 \cdot v \cdot e^{-v} + 766000 \cdot v^9 + (P_{cal} - P_0)$$

The values of parameters C1, C2, C3 and C4 were determined on the basis of numerical optimization, such as the method of least error squares, from a series of tests in which the blood pressure values of various patients in varying exercise conditions and in an upright body position were detected with the aid of a conventional Riva-Rocci blood pressure gauge. By alternative, the values of parameters C1, C2, C3 and C4 can also be fed into the evaluation unit 6 via the input means 11 prior to blood pressure measurement.

The approximate distance D between the heart and the pulse-feeling location 15 may either be measured, estimated or determined on the basis of the patient's body height H, fed in via the input means 11, according to which $$D = K \cdot H \quad (3)$$

with K designating a correlation coefficient that is specific in the respective pulse-feeling location 15. For example, with a pulse-feeling location 15 on the finger of an adult, it is approximately 0.5; and with a pulse-feeling location 15 on a child's toe, it is approximately 0.7. Fundamentally, other regulations of computing the approximate distance D are conceivable apart from the equation (3). For instance, in completion or by alternative of the body height H, the body weight may be admitted just as well.

The first addend in the equation (1) or (2) specifies the active or contractile elasticity behaviour of the blood vessels; the second addend the passive elasticity behaviour, conditioned by the connective tissue, of the blood vessels. The contractile elasticity behaviour is due to the action of the myofilaments and the triggering by means of neural and humoral components. Both elasticities take influence on the propagation of the pulse pressure wave within the blood vessels and thus on the propagation time T which results ultimately. Both kinds of influence partially deviate from each other considerably. The blood pressure gauge 1 takes that into account by use of the various algebraic expressions in the first two addends of the equations (1) and (2).

The third addend in the equation (1) or (2) serves for patient-specific adaptation. That calibration portion is determined by means of a calibration measurement in which the calibration unit 12 detects the calibration blood-pressure value $P_{cal}$ and passes it on to the evaluation unit 6. Along with the calibration measurement by the conventional blood-pressure sensor 13, measurements take place by the ECG sensor 3 and the pulse sensor 4, from which the associated propagation time T of the pulse pressure wave is determined in the evaluation unit 6, and the uncalibrated blood-pressure value $P_0$ by means of the first two addends of the equation (1) or (2). A single calibration measurement will do for patient-specific adaptation (single-point calibration). Of course, further calibration measurements can be made for control of subsequent adjustment purposes.

Figure 4:
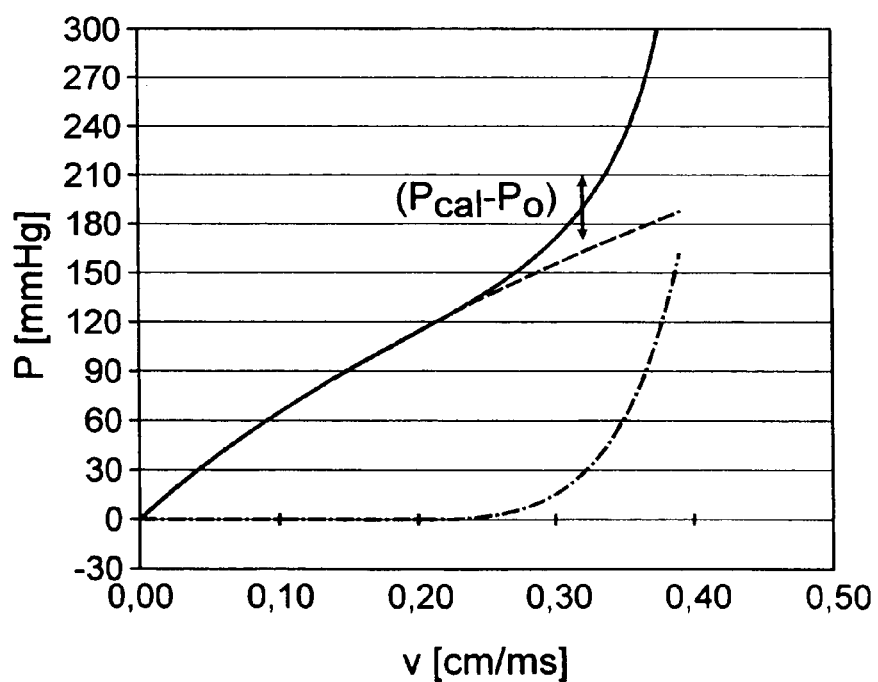
FIG. 4 is a graphic of a nonlinear function interrelationship, on which the FIG. 1 apparatus evaluation bases, between a determined pulse-pressure-wave propagating time and the required blood pressure.

The diagram of FIG. 4 illustrates the first addend of the equation (2) in a dashed line, the second addend of the equation (2) in a dot-dashed line and the sum of both in a solid line. The blood pressure P is plotted over the pulse-pressure-wave velocity v. The difference in influence of the active and the passive portion becomes apparent. While the active portion (=first addend) dominates in the case of low pulse-pressure-wave velocities v and blood pressures P, the passive portion (=second addend) dominates in the case of high pulse-pressure-wave velocities v and blood pressures P. However, both portions contribute to the medium range that applies to the plurality of applications. It is especially that influence of both portions that the known blood pressure determination methods and apparatuses do not comparably make account of. The third addend of the equation (2) delivers an offset i.e., a parallel displacement, related to the v axis, of the cumulative curve (=solid line). That is roughly outlined by the double-headed arrow in FIG. 4.

The blood-pressure-P values thus found are corrected, depending on the body position sensed by the body-position sensor 5. In particular, difference is made between the upright body position, dorsal position, prone position, and the position on the right or left side of a patient's body. In this way, the hydrostatic pressure, which varies in these body positions, is compensated. On the whole, the influence of the hydrostatic pressure that varies along with the body position is not as important in the blood pressure gauge 1 as it is in conventional Riva-Rocci blood pressure determination. This means alleviation of handling and reduced susceptibility to errors of handling. Moreover, in particular with inferior demands on measurement accuracy, it is possible to do without the detection and consideration of the body position.

The above explanations relate to the detection of a systolic-blood-pressure measurement. Detection of the diastolic blood pressure fundamentally works on the same principle.

The blood pressure P detected by the gauge 1 has a high correlation coefficient of at least 0.82 as compared with values made by a conventional Riva-Rocci blood pressure gauge. Moreover, the gauge 1 is excellently apt for long-blood pressure determination, for example for a period of 24 hours. Another advantage resides in that the blood pressure P can be detected virtually continuously i.e., from heartbeat to heartbeat, which is not possible with conventional Riva-Rocci blood pressure gauges.

What is claimed is:

1. A method of noninvasively determining a blood pressure (P) of a patient (2), in which
   a) an electrical cardiac potential measurement signal (EM) is detected;

b) a pulse measurement signal (PM) of a pulse pressure wave which, starting from a patient's heart, propagates within blood vessels is detected at a pulse-feeling location (15);

c) a propagating time (T) of the pulse pressure wave between the heart and the pulse-feeling location (15) is determined, based on the electrical measurement signal (EM) and the pulse measurement signal (PM);

d) wherein the blood pressure (P) is determined from the propagating time (T) by means of a function interrelationship that comprises a first portion specifying an active elasticity behaviour of the blood vessels and a second portion specifying a passive elasticity behaviour of the blood vessels.

2. A method according to claim 1, wherein, in determining the blood pressure, an additional calibration portion is considered in the function interrelationship.

3. A method according to claim 1, wherein a body height of the patient (2) is considered in determining the blood pressure.

4. A method according to claim 1, wherein the electrical measurement signal (EM) and the pulse measurement signal (PM) are detected virtually at the same location.

5. A method according to claim 1, wherein in the function interrelationship the blood pressure determination is based on, use is made of an equation $$P = C1 \cdot \frac{D}{T} \cdot e^{C2 \frac{D}{T}} + C3 \cdot \left(\frac{D}{T}\right)^{C4} + (P_{cal} - P_0)$$

with P being a to-be-determined blood pressure in [mmHg]; with D being an approximate distance in [cm] which the pulse pressure wave covers between the heart and the pulse-feeling location (15); with T being the propagating time of the pulse pressure wave in [ms]; with C1, C2, C3, C4 being a given or selectable parameter; with $P_0$ being a determined, uncalibrated blood pressure value in [mmHg]; and with $P_{cal}$ being a calibration blood pressure value in [mmHg].

6. An apparatus for noninvasively determining of a blood pressure (P) of a patient (2), comprising a) an ECG sensor (3; 18) for detecting an electrical cardiac potential measurement signal (EM);

b) a pulse sensor (4; 19) for detecting a pulse measurement signal (PM) of a pulse pressure wave which, starting from the heart, propagates within the blood vessels as far as to a pulse-feeling location (15) where the pulse sensor (4; 19) is disposed;

c) an evaluation unit (6) for determining a propagation time (T) of the pulse pressure wave between the heart and the pulse-feeling location (15) on the basis of the electrical measurement signal (EM) and the pulse measurement signal (PM);

d) wherein the evaluation unit (6) is designed for determining the blood pressure (P) from the propagating time (T) by means of a function interrelationship which comprises a first portion that specifies the active elasticity behaviour of the blood vessels, and a second portion that specifies the passive elasticity behaviour of the blood vessels.

7. An apparatus according to claim 6, wherein the evaluation unit (6) is designed for consideration of an additional calibration portion, obtained from a calibration measurement, in the blood pressure determination by the function interrelationship.

8. An apparatus according to claim 6, wherein means (11) are provided for input or detection of the body height (H) of the patient (2).

9. An apparatus according to claim 6, wherein the ECG sensor (18) and the pulse sensor (19) are accommodated in a joint detection module (16).

10. An apparatus according to claim 6, wherein an equation for the blood pressure determination function interrelationship is deposited in the evaluation unit (6), according to which $$P = C1 \cdot \frac{D}{T} \cdot e^{C2 \frac{D}{T}} + C3 \cdot \left(\frac{D}{T}\right)^{C4} + (P_{cal} - P_0)$$

with P being the to-be-determined blood pressure in [mmHg]; with D being an approximate distance in [cm] which the pulse pressure wave covers between the heart and the pulse-feeling location (15); with T being the propagating time of the pulse pressure wave in [ms]; with C1, C2, C3, C4 being a given or selectable parameter; with $P_0$ being a determined, uncalibrated blood pressure value in [mmHg]; and with $P_{cal}$ being a calibration blood pressure value in [mmHg].

* * * * *